United States Patent [19]

Brighty et al.

[11] Patent Number: 5,475,116
[45] Date of Patent: Dec. 12, 1995

[54] AZA BICYCLO[3,1,0]HEXANE INTERMEDIATES USEFUL IN THE SYNTHESIS OF QUINOLONES

[75] Inventors: Katherine E. Brighty; Tamim F. Braish, both of Groton, Conn.

[73] Assignee: Pfizer Inc., New York, N.Y.

[21] Appl. No.: 235,434

[22] Filed: Apr. 29, 1994

[51] Int. Cl.⁶ .................................................. C07D 209/52
[52] U.S. Cl. .................................................... 548/452
[58] Field of Search ........................................... 548/252

[56] References Cited

U.S. PATENT DOCUMENTS

| | | | |
|---|---|---|---|
| 5,164,402 | 11/1992 | Brighty | 514/300 |
| 5,229,396 | 7/1993 | Brighty | 514/300 |
| 5,256,791 | 10/1993 | Braish | 548/452 |

*Primary Examiner*—David B. Springer
*Attorney, Agent, or Firm*—Peter C. Richardson; Gregg C. Benson; A. Dean Olson

[57] ABSTRACT

This invention relates to certain azabicyclo hexane intermediates and processes for making and using the azabicyclo hexane intermediates. The intermediates are useful in the synthesis of quinolone antibacterial agents.

11 Claims, No Drawings

AZA BICYCLO[3,1,0]HEXANE INTERMEDIATES USEFUL IN THE SYNTHESIS OF QUINOLONES

BACKGROUND OF THE INVENTION

This invention relates to intermediates, and processes for making and using said intermediates, useful in the synthesis of quinolone antibacterial agents.

The quinolone antibacterial 7-(1α,5α,6α)-(6-amino-3-azabicyclo[3.1.0]hex-3-yl)-1 -(2,4-difluorophenyl)-6-fluoro-1,4-dihydro-4-oxo-1,8-naphthyridine-3-carboxylicacid and related azabicyclo quinolone antibiotic compounds are described in U.S. Pat. Nos. 5,229,396 and 5,164,402. U.S. Pat. No. 5,256,791 discloses processes for the preparation of intermediates useful in the synthesis of these quinolone antibiotics. These intermediates have, for example, the formula

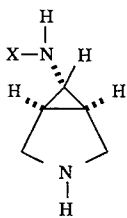

wherein X is a nitrogen protecting group. The foregoing three patents are assigned in common with the present application and are incorporated herein by reference in their entirety.

Thus, there is a continuing search for new intermediates and methods of preparing these quinolone antibacterials.

SUMMARY OF THE INVENTION

The present invention relates to intermediates, useful for the preparation of azabicyclo quinolone antibacterials, having the formula

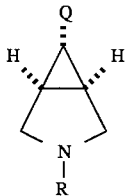

Formula I wherein

R is methyl, $(C_1-C_6)$alkoxycarbonyl, trityl, benzyl, paramethoxybenzyl, paramethylbenzyl, benzoyl, paramethoxybenzoyl, paramethylbenzoyl, benzyloxycarbonyl, paramethoxybenzyloxycarbonyl or paramethylbenzyloxycarbonyl; and Q is —C(=O)$R_1$ or —C(=N—$R_3$)$CH_3$ wherein $R_3$ is hydroxy, tolylsulfonyloxy or methylsulfonyloxy and $R_1$ is amino, hydroxyamino, N,O-dimethyl hydroxyamino, or methyl.

A first group of preferred compounds of Formula I consists of those compounds wherein Q is —C(=O)$R_1$. Within this first group of preferred compounds are especially preferred compounds wherein $R_1$ is amino, N,O-dimethyl hydroxyamino or hydroxyamino. Particularly preferred compounds within the above group of especially preferred compounds are compounds wherein R is benzyl or benzyloxycarbonyl. Within the first group of preferred compounds is a second group of especially preferred compounds wherein $R_1$ is methyl. Particularly preferred compounds within the second group of especially preferred compounds are compounds wherein R is benzyl or benzyloxycarbonyl.

A second group of preferred compounds of Formula I consists of those compounds wherein Q is —C(=N—$R_3$)$CH_3$. Particularly preferred compounds within this second group of preferred compounds are compounds wherein R is benzyl or benzyloxycarbonyl.

Another aspect of this invention is a process for preparing a compound of Formula II

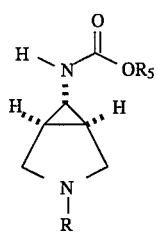

Formula II wherein

R is methyl, $(C_1-C_6)$alkoxycarbonyl, trityl, benzyl, paramethoxybenzyl, paramethylbenzyl, benzoyl, paramethoxybenzoyl, paramethylbenzoyl, benzyloxycarbonyl, paramethoxybenzyloxycarbonyl or paramethylbenzyloxycarbonyl; and $R_5$ is $(C_1-C_6)$alkyl comprising:

reacting a compound of Formula IB

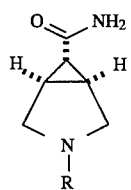

Formula IB wherein

R is methyl, $(C_1-C_6)$alkoxycarbonyl, trityl, benzyl, paramethoxybenzyl, paramethylbenzyl, benzoyl, paramethoxybenzoyl, paramethylbenzoyl, benzyloxycarbonyl, paramethoxybenzyloxycarbonyl or paramethylbenzyloxycarbonyl with iodobenzene diacetate or iodobenzene bis(trifluoroacetate) in a $(C_1-C_6)$alcohol in the presence of sodium or potassium $(C_1-C_6)$alkoxide or sodium or potassium hydroxide at a temperature of about –20° C. to about 10° C., followed by reaction at a temperature of about 10° C. to about 40° C.

In the process for making Formula II compounds it is preferred that iodobenzene diacetate, methanol and sodium methoxide are used and especially preferred that R is benzoyl.

Yet another aspect of this invention is a second process for preparing a compound of Formula II

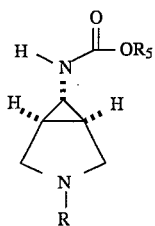

Formula II wherein

R is methyl, (C$_1$–C$_6$)alkoxycarbonyl, trityl, benzyl, paramethoxybenzyl, paramethylbenzyl, benzoyl, paramethoxybenzoyl, paramethylbenzoyl, benzyloxycarbonyl, paramethoxybenzyloxycarbonyl or paramethylbenzyloxycarbonyl; and R$_5$ is (C$_1$–C$_6$)alkyl comprising:
reacting a compound of Formula IA

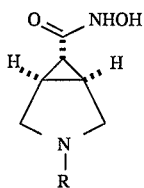

Formula IA wherein

R is methyl, (C$_1$–C$_6$)alkoxycarbonyl, trityl, benzyl, paramethoxybenzyl, paramethylbenzyl, benzoyl, paramethoxybenzoyl, paramethylbenzoyl, benzyloxycarbonyl, paramethoxybenzyloxycarbonyl or paramethylbenzyloxycarbonyl; with (C$_1$–C$_6$)alkylsulfonyl chloride, benzenesulfonyl chloride or p-toluenesulfonyl chloride in an amine base at a temperature of about 0° C. to about 40° C., followed by reaction with a (C$_1$–C$_6$) alcohol at a temperature of about ambient to about 85° C.

In the second process for making Formula II compounds it is preferred that p-toluenesulfonyl chloride, pyridine and tert-butanol are used, and that the reaction is performed at ambient temperature, followed by reaction at a temperature of about 70° to 85° C. It is especially preferred that R is benzyloxycarbonyl.

Yet another aspect of this invention is a process for preparing a compound of Formula VIII

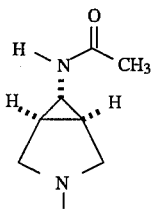

Formula VIII wherein

R is methyl, (C$_1$–C$_6$)alkoxycarbonyl, trityl, benzyl, paramethoxybenzyl, paramethylbenzyl, benzoyl, paramethoxybenzoyl, paramethylbenzoyl, benzyloxycarbonyl, paramethoxybenzyloxycarbonyl or paramethylbenzyloxycarbonyl; comprising:

a. reacting a compound of Formula VI

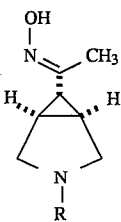

Formula VI wherein

R is methyl, (C$_1$–C$_6$)alkoxycarbonyl, trityl, benzyl, paramethoxybenzyl, paramethylbenzyl, benzoyl, paramethoxybenzoyl, paramethylbenzoyl, benzyloxycarbonyl, paramethoxybenzyloxycarbonyl or paramethylbenzyloxycarbonyl with p-toluenesulfonyl chloride or methanesulfonyl chloride in a halogenated organic solvent/amine-base mixture at a temperature of about −20° C. to about 10° C. followed by warming to a temperature of about 10° C. to about 40° C.; and b. reacting said product with sodium or potassium carbonate or an amine base in aqueous tetrahydrofuran or aqueous (C$_1$–C$_6$) alcohol at a temperature of about 50° C. to about 95° C.

In the process for making Formula VIII compounds it is preferred that p-toluenesulfonyl chloride, pyridine and dichloromethane are used and especially preferred that R is benzyloxycarbonyl.

By alkyl is meant straight chain or branched hydrocarbon.

Other features and advantages will be apparent from the specification and claims which describe the invention.

DETAILED DESCRIPTION OF THE INVENTION

The processes of the present invention and the preparation of the compounds of the present invention are illustrated in the following reaction schemes.

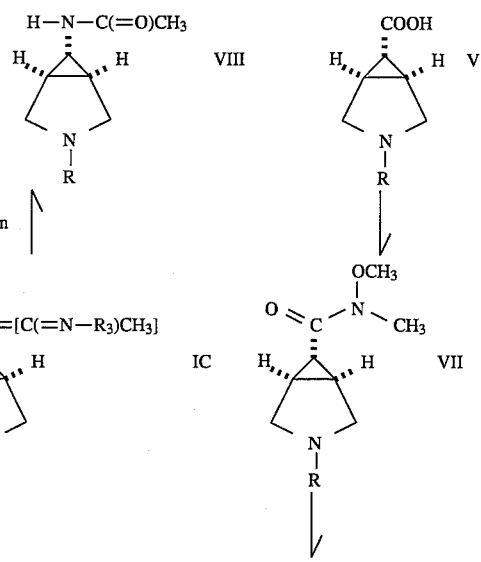

Scheme I

-continued
Scheme I

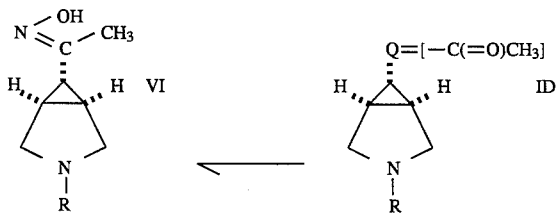

Scheme II

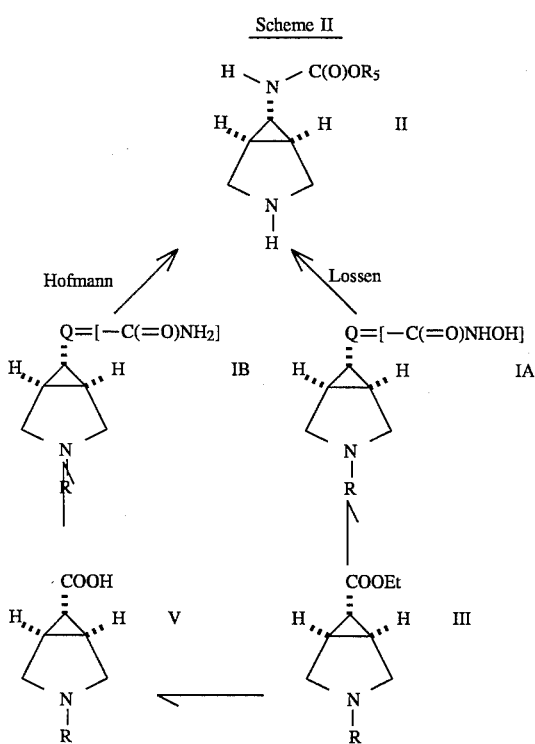

According to Reaction Scheme II the desired Formula II compounds wherein R and $R_5$ are as defined above may be prepared from the appropriate Formula IA compounds wherein R is as defined above (e.g., Formula I compounds wherein Q is—C(=O)NHOH) by a Lossen rearrangement.

Typically the Formula IA compound is reacted with alkyl or aryl or aryl substituted sulfonyl chlorides, for example benzenesulfonyl chloride, p-toluenesulfonyl chloride or ($C_1$–$C_6$)alkylsulfonyl chloride (e.g., methanesulfonyl chloride) in an amine base, for example pyridine, at a temperature of about 0° C. to about 40° C. followed by reaction with a ($C_1$–$C_6$) alcohol (i.e., ($C_1$–$C_6$)alkanol) at a temperature of about ambient to about 85° C., preferably about 70° to 85° C.

The desired Formula IA compounds wherein R is as defined above may be prepared from the appropriate Formula III compounds wherein R is as defined above by amidation.

Typically the Formula III compound is reacted with hydroxylamine hydrochloride in the presence of a base, such as potassium hydroxide, in a protic solvent such as a ($C_1$–$C_6$)alcohol at a temperature of less than about 40° C., preferably less than about 25° C.

Alternatively, the desired Formula II compounds wherein R and $R_5$ are as defined above may be prepared from the appropriate Formula IB compounds wherein R is as defined above (e.g., Formula I compounds wherein Q is —C(=O)NH_2) via a Hofmann rearrangement.

Generally the Formula IB compound is reacted with iodobenzene diacetate or iodobenzene bis(trifluoroacetate) in a polar solvent such as a ($C_1$–$C_6$)alcohol, preferably methanol, in the presence of a base such as a metal alkoxide, typically sodium or potassium ($C_1$–$C_6$)alkoxide, or a metal hydroxide such as sodium or potassium hydroxide at a temperature of about –20° C. to about 10° C. for about one hour to about eight hours, followed by reaction at a temperature of about 10° C. to about 40° C. for about one hour to about twenty hours.

The desired Formula IB compounds wherein R is as defined above may be prepared by amidation (via activation of the acid followed by ammonolysis) of the appropriate Formula V compound wherein R is as defined above.

Typically, according to one procedure, the Formula V compound is combined with thionyl chloride at elevated temperatures, such as about 50° C. to about 125° C. for about one hour to about six hours. The resulting product is dissolved in an inert solvent such as toluene and exposed (e.g., by sparging) to ammonia gas for about one minute to about thirty minutes followed by stirring for about one hour to about ten hours at a temperature of about ambient to about 50° C.

According to an alternative procedure, the Formula V compound is dissolved in a non-nucleophilic solvent such as tetrahydrofuran and carbonyldiimidazole is added followed by stirring for about three hours to about eight hours at a temperature of about ambient to about 50 ° C. Then the reaction is exposed to ammonia gas for about one minute to about thirty minutes followed by stirring for about one hour to about ten hours at a temperature of about ambient to about 50° C.

The desired Formula V compound wherein R is as defined above may be prepared from the appropriate Formula III compound by hydrolysis.

Generally, the Formula III compound is combined with excess acid, such as a mineral acid, preferably hydrochloric acid for about one to about five hours at a temperature of about ambient to about reflux. Alternatively, the Formula III compound is dissolved in an alcohol/water mixture solvent such as alcohol/water and combined with a strong base such as lithium hydroxide at a temperature of about ambient to about 50° C. for about three hours to about twenty-four hours followed by acidification to isolate the carboxylic acid.

The desired Formula III compound wherein R is as defined above may be prepared from the corresponding N-benzyl-2,4-dioxo analog by reduction, or by a three step process including reduction, deprotection of the amine (hydrogenation) and acylation (protection of the amine).

The corresponding 2,4-dioxo analog of the Formula III compound is reduced by combining a reducing agent such as sodium borohydride and boron trifluoride etherate in an etheral solvent such as tetrahydrofuran at a temperature below about 15° C. with the 2,4-dioxo analog and maintaining the temperature below about 15° C. for about thirty minutes to about five hours. The resulting reduced compound can then have its amine hydrogenated by exposure to hydrogen in the presence of a noble metal such as palladium at elevated pressures for about twenty-four hours. The amine functionality is reprotected by reaction with benzyl chloroformate in the presence of an amine base such as triethylamine in an inert solvent such as methylene chloride at ambient temperature to about reflux for about three hours to about twenty-four hours.

According to Reaction Scheme I the desired Formula VIII compounds wherein R is as defined above may be prepared from the appropriate Formula IC compounds wherein R and $R_3$ are as defined above (e.g., Formula I compounds wherein Q is —C(=N—$R_3$)CH$_3$) via a Beckmann rearrangement.

Typically, the Formula IC compound is combined with a base such as an amine or potassium or sodium carbonate in an aqueous/polar solvent solution, such as aqueous tetrahydrofuran or aqueous ($C_1$–$C_6$)alcohol, at a temperature of about 40° C. to about reflux, preferably about 50° C. to about 95° C. for about one to about eight hours.

The desired Formula IC compounds wherein R and $R_3$ are as defined above may be prepared from the appropriate Formula VI compound wherein R is as defined above by reaction with an alkyl, aryl or aryl-substituted sulfonyl chloride such as ($C_1C_6$) alkylsulfonyl chloride, benzenesulfonyl chloride or p-toluenesulfonyl chloride.

Typically, the Formula VI compound is reacted with a sulfonyl chloride such as p-toluenesulfonyl chloride or methanesulfonyl chloride in a halogenated aprotic solvent/amine-base mixture at a temperature of about −20° C. to about 10° C. for about 15 minutes to about three hours followed by warming to about 10° C. to about 40° C. for about five hours to about twenty hours. An exemplary halogenated organic solvent is dichloromethane and an exemplary amine-base is pyridine.

The desired Formula VI compounds wherein R is as defined above may be prepared from the appropriate Formula ID compound wherein R is as defined above (i.e. Formula I compounds wherein Q is —C(=O)CH$_3$) by standard oxime formation.

Generally, the Formula ID compound is reacted with hydroxylamine hydrochloride in a suitable solvent such as an amine base, particularly pyridine, for about twenty-four to about seventy-two hours at a temperature of about ambient to about 50° C.

The desired Formula ID compounds wherein R is as defined above may be prepared from the appropriate Formula VII compound wherein R is as defined above by addition of an alkyl group to the amide (e.g., procedure of Weinreb (Tetrahedron Lett. (81)22 3815)).

Typically, the Formula VII compound is reacted with a solvent solution (e.g., diethyl ether) of methylmagnesium bromide at a temperature of about −10° C. to about ambient for about three to about fifteen hours in a ethereal solvent such as tetrahydrofuran.

The desired Formula VII compounds wherein R is as defined above may be prepared from the appropriate Formula V compound wherein R is as defined above by amide formation.

Typically, the Formula V compound is activated with carbonyldiimidazole in an inert solvent such as tetrahydrofuran at a temperature of about 15° C. to about 45° C. for about thirty minutes to about five hours. The resulting compound is diluted with a chlorinated solvent such as dichloromethane and cooled to a temperature of about −15° C. to about 15° C. and treated, preferably sequentially, with an amine base such as triethylamine and N,O-dimethylhydroxylamine hydrochloride while warming to about ambient temperature for about five to about twenty-four hours.

The R group in Formula II and VIII compounds may be removed by methods familiar to those skilled in the art (T. W. Greene and P. G. M. Wuts, Protective Groups in Organic Synthesis Wiley & Sons, 1991 ).

The starting materials and reagents for the above described reaction schemes are readily available or can be easily synthesized by those skilled in the art using conventional methods of organic synthesis.

If necessary, the compounds which have been obtained and have configurational isomers can be separated into their isomers on the basis of their physical chemical differences by methods known per se, for example, by chromatography and/or fractional crystallization.

The methods by which the compounds of this invention may be converted into the antibiotics are set forth in detail in U.S. Pat. Nos. 5,229,396 and 5,164,402.

The antibacterial compound described in the Background of the Invention section and the related azabicyclo quinolone carboxylic acid antibacterial agents that can be synthesized using the methods and compounds of this invention are useful in the treatment of animals, including humans, having bacterial infections. They are useful in treating bacterial infections of broad spectrum, particularly in treating gram-positive bacterial strains.

U.S. Pat. Nos. 5,229,396 and 5,164,402 set forth in detail the appropriate dosage ranges and methods of administration of such antibacterial compounds. These references also set forth a method by which the antibacterial activity of such compounds may be determined.

It should be understood that the invention is not limited to the particular embodiments shown and described herein, but that various changes and modifications may be made without departing from the spirit and scope of this novel concept as defined by the following claims.

EXAMPLE 1

(1α,5α,6α)-benzyl-3-azabicyclo[3.1.0]hexane-6-carboxylic acid, ethyl ester

Sodium borohydride (13.1 g, 0.35 moles) in 300 ml of THF was cooled to 0° C. and boron trifluoride etherate (65.8 g, 0.46 moles) was added dropwise over a period of 30 min. (1α,5α,6α)-2,4-Dioxo-3-benzyl-3-azabicyclo [3.1.0]hexane-6-carboxylic acid, ethyl ester (30.0 g, 0.12 moles) was then added as a solution in 187 ml of THF. The reaction was kept at 0° C. for two hours and was then carefully quenched with 375 ml of ethanol. The reaction was heated to reflux for 30 min and then the solvents were evaporated. The residue was dissolved in 300 ml of CH$_2$Cl$_2$ and washed with 150 ml of water. The aq. layer was extracted with 75 ml of CH$_2$Cl$_2$ and the combined organic layers were dried and evaporated to an oil which weighed 25.5 g (87%). NMR(CDCl$_3$): 7.2–7.4 (m, 5H, aromatic), 4.1(q, 2H, ethyl ester),3.6(s, br, 2H), 3.05(d, 2H), 2.42 (d, 2H), .90 (broad, 1H), 1.3 (m, 2H, cyclopropyl), 1.25 (t, 3H, methyl).

EXAMPLE 2

(1α,5α,6α)-3-azabicyclo[3.1.0]hexanecarboxylic acid, ethyl ester (1α,5α,6α)-3-benzyl-3-azabicyclo[3.1.0]hexane-6-carboxylic acid, ethyl ester (8.18 g, 0.03 moles) was dissolved in 164 ml of ethanol and 4.05 g of palladium hydroxide was added. The mixture was hydrogenated on a Parr shaker with 50 PSI hydrogen pressure for 24 hours. The reaction was filtered through celite and the solvent was evaporated to provide an oil weighing 4.33 g (93%). NMR(CDCl$_3$): 4.1 (q, 2H, ester), 3.04 (d, 2H), 2.90 (d, 2H), 2.5 (br, 1H, amine H), 1.95 (br, 1H), 1.40(m, 2H), 1.22 (t, 3H, methyl).

EXAMPLE 3

(1α,5α,6α)-3-carbobenzyloxy-3-azabicyclo [3.1.0]hexane-6-carboxylic acid, ethyl ester (1α,5α,6α)-3-azabicyclo[3.1.0]hexane-6-carboxylic acid, ethyl ester (2.22 g, 14.3 mmol) was dissolved in 50 ml of $CH_2Cl_2$ and triethylamine (1.74 g, 17.18 mmol) was added along with benzyl chloroformate (2.69 g, 15.7 mmol). The reaction was stirred at room temperature for 16 h. The reaction was diluted with 25 ml of $CH_2Cl_2$ and was washed with 25 ml of 10% aq. HCl solution. The organic layer was dried over $MgSO_4$ and evaporated to obtain 3.59 g of an oil which was chromatographed on silica gel using 25% ethyl acetate in hexane. The reaction yielded 2.04 g of the desired product in 49% yield. $NMR(CDCl_3)$: 7.40 (m, 5H, aromatic), 5.10 (s, 2H, benzyl), 4.12 (q, 2H, ethyl group), 3.75 (m, 2H), 3.50 (m, 2H), 2.10 (m, 2H), 1.50 (m, 1H), 1.25 (t, 3H methyl).

EXAMPLE 4

(1α,5α,6α)-3-carbobenzyloxy-3-azabicyclo [3.1.0]hexane-6-carboxylic acid (1α,5α,6α)-3-carbobenzyloxy-3-azabicyclo [3.1.0]hexane-6-carboxylic acid, ethyl ester (1.77 g, 6.12 mmol) was dissolved in 50 ml of methanol and 50 ml of water and lithium hydroxide hydrate (771 mg, 18.36 mmol) was added. The mixture was allowed to stir at room temperature for 16 h (overnight). The methanol was removed under vacuum and the pH of the residue was adjusted to 2 using 10% aq. HCl solution. Extraction with 3×30 ml of $CH_2Cl_2$ followed by drying and evaporation provided 1.28 g of the desired product in 80% yield. $NMR(CDCl_3)$: 7.35–7.40 (m, 5H, aromatic), 5.10(s, 2H, benzyl), 3.75 (m, 2H), 3.52 (m, 2H), 2.18 (m, 2H), 1.5 (m, 1H).

EXAMPLE 5

(1α,5α,6α)-3-carbobenzyloxy-3-azabicyclo[3.1.0]hexane-6-carboxamide (1α,5α,6α)-3-carbobenzyloxy-3-azabicyclo[3.1.0]hexane-6-carboxylic acid (680 mg, 2.60 mmol) was dissolved in 100 ml of THF and carbonyldiimidazole (464 mg, 2.86 mmol) was added. The reaction was allowed to stir at room temperature for 5 h after which ammonia gas was bubbled through the reaction for 5 min. The reaction was then allowed to stir overnight (16 h). The reaction was judged complete by TLC and 100 ml of water was added. The mixture was extracted with 3×100 ml of $CH_2Cl_2$ and the combined organic layers were dried and evaporated to obtain 280 mg of the desired product (41% yield). $NMR(CDCl_3)$: 7.35–7.40 (m, 5H, aromatic), 5.7–6.0 (Broad, 2H, amide protons), 5.10(s, 2H, benzylic), 3.70(m, 2H), 3.50(m, 2H), 2.18(m, 2H) 1.5(m, 1H).

EXAMPLE 6

(1α,5α,6α)-3-carbobenzyloxy-6-methoxycarbonylamino-3-azabicyclo [3.1.0]hexane (1α,5α,6α)-3-carbobenzyloxy-3-azabicyclo[3.1.0]hexane-6-carboxamide (50 mg, 0.19 mmol) was dissolved in 1 ml of methanol and iodobenzene diacetate (93 mg, 0.29 mmol) was added. The mixture was cooled to 0° C. and excess sodium methoxide in 1 ml of methanol was added and the mixture was allowed to stir at 0° C. for 4 h and at room temperature for 16 h. Acidification of the reaction to pH 2 was accomplished using 10% aq. HCl and this was followed by removing the methanol under vacuum. The residue was extracted with 3×4 ml of $CH_2Cl_2$ and the combined organic layers were dried and evaporated to obtain the desired product. The product was isolated via chromatography using 60% ethyl acetate in hexane. $NMR(CDCl_3)$: 7.30–7.35 (m, 5H, aromatic), 5.10 (s, 2H, benzylic), 4.9 (broad, 1H, nitrogen), 3.70 (m, 5H, [2H 5-ring an methyl]), 3.50 (m, 2H), 1.27 (m, 2H), 0.9 (m, 1H).

EXAMPLE 7

(1α,5α,6α)-3-benzyl-3-azabicyclo [3.1.0]hexane-6-carboxylic acid, (1α,5α,6α)-3-benzyl-3-azabicyclo [3.1.0]hexane-6-carboxylic acid, ethyl ester (25 g, 104 mmol) was suspended in 46 ml of 20% aq. hydrochloric acid solution and heated to reflux for 3.5 h. The reaction was then allowed to cool to room temperature and stir overnight. The solids were filtered and dried in a vacuum oven to obtain 15 g of product (57% yield). M.p.=240°–242° C. $NMR(CDCl_3)$: 7.40–7.70 (m, 5H, aromatic), 4.31 (m, 2H), 3.45 (m, 4H), 2.5 (m, 1H), 2.12 (m, 2H).

EXAMPLE 8

(1α,5α,6α)-3-benzyl-3-azabicyclo[3.1.0]hexane-6-carboxamide

To (1α,5α,6α)-3-benzyl-3-azabicyclo[3.1.0]hexane-6-carboxylicacid(6.63g,26.13 mmol) was added 28.6 ml of thionyl chloride and the mixture was heated to 85° C. for 3 h. The reaction was allowed to cool to room temperature and stirred for 16 h. The excess thionyl chloride was removed under vacuum and toluene was added and evaporated to remove remaining traces of thionyl chloride. The residue was suspended in 100 ml of toluene and ammonia gas was allowed to bubble through the reaction for 4 min. After stirring for 24 h at room temperature, 15 ml of water was added and the product was filtered and dried at high vacuum to obtain 3.71 g of the amide (41% yield). $NMR(CDCl_3)$: 7.20–7.36 (m, 5H, aromatic), 6.73 (m, 2H amide), 3.60 (broad s, 2H), 2.90 (m, 2H), 2.40 (m, 2H), 1.91 (m, 1H), 1.70 (m, 2H).

EXAMPLE 9

(1α,5α,6α)-3-benzyl-6-methoxycarbonylamino-3-azabicyclo [3.1.0]hexane:

(1α,5α,6α)-3-benzyl-3-azabicyclo[3.1.0]hexane-6-carboxamide (300 mg, 1.39 mmol) was dissolved in 15 ml of methanol and bis acetate iodobenzene (671 mg, 2.08 mmol) was added at 0° C. To that, excess sodium methoxide was added and the mixture was allowed to stir at 0° C. for 3 h and at room temperature for 16 h. The reaction was acidified to pH 2 with aq 10 % HCl solution and the methanol was removed under vacuum. 20 ml of water was added to the residue and the mixture was extracted with methylene chloride (3×10) ml. The combined organic layers were dried and evaporated to give an oil which was chromatographed on silica gel using 50% ethyl acetate in hexane. 30 mg of the product were obtained. $NMR(CDCl_3)$: 7.3"7.15 (m, 5H, aromatic), 3.65 (broad s, 2H, benzylic), 3.59 (s, 3H, methyl), 3.08 (d, 2H), 2.40 (d, 2H), 2.38 (s, 1H), 1.52 (m, 2H).

EXAMPLE 10

[1α,5α,6α]-3-Benzyloxycarbonyl-N-hydroxy-3-azabicyclo [3.1.0]hexane-6-carboxamide A chilled mixture of hydroxylamine hydrochloride (90 mg, 1.3 mmol) and potassium hydroxide (145 mg, 2.6 mmol) in ethanol (3.5 ml) was added dropwise to an ice-cooled solution of ethyl [1α,5α,6α]-3-benzyloxycarbonyl-3azabicyclo [3.1.0]hexane-6-carboxylate (250 mg, 0.86 mmol) [prepared as in U.S. Pat. No. 5,229,396] in ethanol (3 ml). After 3 hours, the reaction was filtered and the filtrate concentrated in vacuo. Water was added to the residue, and the mixture was acidified to pH 3 with 6N hydrochloric acid, then extracted three times with dichloromethane. The combined organic layers were dried over sodium sulfate, filtered and concentrated. Trituration of the resulting oil with diethyl ether provided the title product as a white powder (70 mg, 0.25 mmol, 29% yield) which was used without further purification.

$^1$NMR (CDCl$_3$/MeOH-d$_4$): 7.28 (bs, 5H), 6.00 (s, 2H), 3.59 (bd, J=11 Hz, 2H), 3.43(dd, J=4, 11 Hz, 2H), 2.01 (bs, 2H), 1.10 (bs, 1H).

EXAMPLE 11

[1α,5α,6α]-3-Benzyloxycarbonyl-6-tert-butoxycarbonylamino 3-azabicyclo [3.1.0]hexane A solution of [1α,5α,6α]-3-benzyloxycarbonyl-N-hydroxy-3-azabicyclo[3.1.0]-hexane- 6-carboxamide (0.20 g, 0.724 mmol) in pyridine (5 ml) was added dropwise to a solution of p-toluenesulfonyl chloride (0.41 g mg, 2.17 mmol) in pyridine (15 ml). After 30 min, this solution was added over 20 rain to a refluxing solution of tert-butanol (20 ml) and toluene (20 ml). After five hours, the reaction was allowed to cool, washed with aqueous sodium bicarbonate solution, and extracted with dichloromethane (3×100 ml). The combined organic layers were dried over sodium sulfate, filtered and concentrated in vacuo to give a brown oil. Silica gel column chromatography (eluant: 35% ethyl acetate/65% hexane) provided the title product as a colorless oil (104 mg, 0.31 mmol, 43% yield).

$^1$NMR (CDCl$_3$): 7.31 (bs, 5H), 5.08 (s, 2H), 4.82 (bs, 1H), 3.71(m, 2H), 3.46 (m, 2H), 2.27 (bs, 1H), 1.68 (bs, 2H), 1.43 (s, 9H).

EXAMPLE 12

[1α,5α,6α]-3-Benzyloxycarbonyl-N-methoxy-N-methyl-3-azabicyclo-[3.1.0 ]hexane-6-carboxamide To a solution of [1α,5α, 6α]-3-benzyloxycarbonyl-3-azabicyclo[3.1.0]hexane-6 carboxylic acid [prepared according to U.S. Pat. No. 5,229,396] (1.5 g, 5.74 mmol) in tetrahydrofuran (25 ml) was added carbonyldiimidazole (930 mg, 5.74 mmol). The reaction was allowed to stir at ambient temperature for 2 hours, then was diluted with dichloromethane (25 ml) and cooled to 0° C. After sequential treatment with triethylamine (1.76 ml) and N,O-dimethylhydroxylamine hydrochloride (616 mg, 6.32 mmol), the reaction mixture was allowed to warm to room temperature and stir for 18 hours. The reaction was then poured into water and extracted with chloroform. The combined organic layers were dried over sodium sulfate, filtered and concentrated to give the crude product. Purification via silica gel column chromatography (eluant: chloroform) gave the title product as a colorless oil (940 mg, 3.1 mmol, 54% yield).

$^1$NMR (CDCl$_3$): 7.48 (bs, 5H), 5.14 (apparent d (actually AB quartet), J=2 Hz, 2H), 3.72 (s, 3H), 3.7 (m, 2H), 3.55 (m, 2H), 3.21 (s, 3H), 2.10 (m, 2H), 1.98 (m, 1H).

EXAMPLE 13

1-([1α,5α,6α]-3-Benzyloxycarbonyl-3-azabicyclo[3.1.0] hex-6-yl)-ethanone

To a solution of [1α,5α,6α]-3-benzyloxycarbonyl-N-methoxy-N-methyl-3-azabicyclo[3.1.0.] ]hexane-6-carboxamide (940 mg, 3.1 mmol) in tetrahydrofuran (30 ml) at 0 ° C. was added methylmagnesium bromide (3.0 M solution in diethyl ether, 3.1 ml, 9.3 mmol). The reaction mixture was allowed to warm to room temperature and stir for 10 hours, after which it was poured into water and extracted with diethyl ether. The combined organic layers were washed with saturated sodium chloride solution, dried over sodium sulfate, filtered and concentrated to provide crude product. Purification via silica gel column chromatography (eluant: 20% ethyl acetate/80% chloroform) provided the title product as a white solid, mp 90°–91° C. (570 mg, 2.2 mmol, 71% yield). $^1$H NMR (CDCl$_3$): 7.35 (m, 5H), 5.11 (s, 2H), 3.75 (d, J=11 Hz, 1H), 3.70 (d, J=11 Hz, 1H), 3.49 (m, 2H), 2.25 (s, 3H), 2.10 (m, 2H), 1.80 (t, J=3 Hz, 1H).

EXAMPLE 14

(E)-1-([1α,5α,6α]-3-Benzyloxycarbonyl-3-azabicyclo [3.1.0]hex-6-yl )-ethanone oxime Hydroxylamine hydrochloride (94 mg, 1.34 mmol) and 1 -([1α,5α,6α]-3-benzyloxycarbonyl- 3-azabicyclo[3.1.0] hex-6-yl)-ethanone (320 mg, 1.23 mmol) were combined in pyridine (3 ml) and the reaction mixture allowed to stir for 48 hours. The reaction was then poured into water and extracted with chloroform. The organic layers were combined, washed twice with water, once with saturated sodium chloride solution and dried over sodium sulfate. Filtration and removal of solvent in vacuo provided crude material, which was purified via silica gel column chromatography (eluant: 10% ethyl acetate/90% chloroform) to provide both isomers of the title product as white solids:

(E)-oxime (180 mg, 0.66 mmol, 54% yield) $^1$H NMR (CDCl$_3$): 7.36 (bs, 5H), 7.14 (s, 1H), 5.12 (s, 2H), 3.75 (d, J=11 Hz,1H) 370(d, J=11 Hz, 1H), 3.46 (m, 2H), 1.88 (m, 2H), 1.82 (s, 3H), 1.35 (t, J=4 Hz, 1H).

(Z)-oxime, mp 105°–106 ° C. (40 mg, 0.15 mmol, 12% yield) $^1$H NMR (CDCl$_3$): 9.25 (bs, 1H), 7.35 (bs, 5H), 5.09 (AB quartet, J=11 Hz, 2H), 3.79 (d, J=11 Hz, 1H), 3.72 (d, J=11 Hz, 1H), 3.50 (m, 2H), 2.29 (t, J=4 Hz, 1H), 1.90 (m, 2H), 1.51 (s, 3H).

EXAMPLE 15

(E)-1 ([1α,5α,6α]-3-Benzyloxycarbonyl-3-azabicyclo [3.1.0]hex-6-yl)-ethanone

O-[(4-methylphenyl)sulfonyl]-oxime p-Toluenesulfonyl chloride (163 mg, 0.85 mmol) in dichloromethane (2 ml) was added dropwise over 1 hour to a 0° C. mixture of (E)-1-([1α,5α,6α]- 3-benzyloxycarbonyl-3-azabicyclo [3.1.0]hex-6-yl)- ethanone oxime and its Z-isomer (3.5:1 mixture, 130 mg, 0.47 mmol) dissolved in dichloromethane (5 ml) and pyridine (0.69 ml, 0.93 mmol). After the reaction had warmed to ambient temperature and stirred for 18 hours, it was poured into 1N hydrochloric acid, then extracted with chloroform. The combined organic extracts were washed with sodium bicarbonate solution and saturated sodium chloride solution, then dried over sodium sulfate. Filtration and removal of solvent in vacuo gave a crude product which was purified by silica gel column chromatography (eluant: 10% ethyl acetate/90% chloroform) to provide the (E)- and (Z)-isomers of the title product.

(E)-oxime tosylate, (80 mg, 0.19 mmol, 40% yield) $^1$H NMR (CDCl$_3$): 7.82 (d, J=8 Hz, 2H), 7.34 (bs, 5H), 7.34 (d, J=8 Hz, 2H), 5.10 (s, 2H), 3.69 (m, 2H), 3.44 (m, 2H), 2.47 (s, 3H), 1.9 (m, 2H), 1.89 (s, 3H), 1.40 (t, J=4 Hz, 1H). Hz, 1H).

(Z)-oxime tosylate (20 mg, 0.047 mmol, 10% yield) $^1$H NMR (CDCl$_3$): 7.86 (d, J=8 Hz, 2H), 7.37 (m, 7H), 5.14 (AB quartet, J=11 Hz, 2H), 3.72 (m, 2H), 3.49 (m, 2H), 2.46 (s, 3H), 2.18 (t, J=4 Hz, 1H), 1.96 (m, 2H), 1.64 (s, 3H).

EXAMPLE 16

N-([1α,5α,6α]-3-Benzyloxycarbonyl-3-azabicyclo[3.1.0]hex-6-yl)-acetamide

A mixture of (E)-1-([1α,5α,6α]-3-benzyloxycarbonyl-3-azabicyclo[3.1.0]hex-6-yl)-ethanone O-[(4-methylphenyl)sulfonyl]-oxime (80 mg, 0.19 mmol) and potassium carbonate (76 mg, 0.47 mmol) in water (4 ml) and tetrahydrofuran (0.5 ml) was heated to 75° C. for 4 hours. The reaction mixture was then extracted with chloroform after cooling, and the combined organic layers dried over sodium sulfate, filtered and concentrated in vacuo to provide the title product as a white solid (40 mg, 0.15 mmol, 79% yield).

$^1$H NMR (CDCl$_3$): 7.32 (bs, 5H), 6.04 (bs, 1H), 5.07 (s, 2H), 3.73 (m, 2H), 3.45 (m, 2H), 2.40 (m, 1H), 1.89 (s, 3H), 1.67 (m, 2H).

I claim:

1. A compound of Formula I

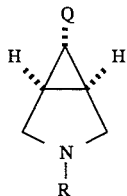

Formula I wherein

R is methyl, (C$_1$–C$_6$)alkoxycarbonyl, trityl, benzyl, paramethoxybenzyl, paramethylbenzyl, benzoyl, paramethoxybenzoyl, paramethylbenzoyl, benzyloxycarbonyl, paramethoxybenzyloxycarbonyl or paramethylbenzyloxycarbonyl; and Q is —C(=O)R$_1$ or —C(=N—R$_3$)CH$_3$ wherein R$_3$ is hydroxy, tolylsulfonyloxy or methylsulfonyloxy and R$_1$ is amino, hydroxyamino, N,O-dimethyl hydroxyamino, or methyl.

2. The compound as recited in claim 1 wherein Q is —C(=O)R$_1$.

3. The compound as recited in claim 2 wherein R$_1$ is amino, N,O-dimethyl hydroxyamino or hydroxyamino.

4. The compound as recited in claim 3 wherein R is benzyl.

5. The compound as recited in claim 3 wherein R is benzyloxycarbonyl.

6. The compound as recited in claim 2 wherein R$_1$ is methyl.

7. The compound as recited in claim 6 wherein R is benzyl.

8. The compound as recited in claim 6 wherein R is benzyloxycarbonyl.

9. The compound as recited in claim 1 wherein Q is —C(=N—R$_3$)CH$_3$.

10. The compound as recited in claim 9 wherein R is benzyl.

11. The compound as recited in claim 9 wherein R is benzyloxycarbonyl.

* * * * *